United States Patent
Fujimura et al.

[11] Patent Number: 5,939,078
[45] Date of Patent: Aug. 17, 1999

[54] WRINKLE-CARE PRODUCT

[75] Inventors: Tsutomu Fujimura; Ayumi Ogawa; Kazue Tsukahara; Yoshinori Takema; Minoru Nagai; Toshiya Ono, all of Tochigi, Japan

[73] Assignee: Kao Corporation, Tokyo, Japan

[21] Appl. No.: 08/746,808

[22] Filed: Nov. 18, 1996

[30] Foreign Application Priority Data

Nov. 20, 1995 [JP] Japan .................................. 7-301524

[51] Int. Cl.$^6$ ...................................................... A61K 7/48
[52] U.S. Cl. ......................... 424/401; 514/634; 514/844; 514/845; 514/846; 514/944
[58] Field of Search ........................ 424/401; 514/634, 514/844, 845, 846, 944

[56] References Cited

PUBLICATIONS

Chemical Abstracts CA 124:316542 (1996).

*Primary Examiner*—Jyothsna Venkat
*Attorney, Agent, or Firm*—Oblon, Spivak, McClelland, Maier & Neustadt, P.C.

[57] ABSTRACT

A wrinkle-care product, an aging-preventive cosmetic and a skin cosmetic each comprising a guanidine derivative of formula (I) or an acid addition salt thereof:

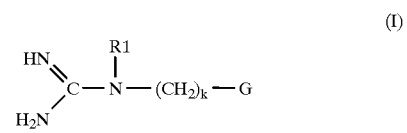

wherein R1 represents a hydrogen atom, a lower alkyl group or —(AO)$_m$—(BO)$_n$—D—E [wherein A and B may be the same or different and each represents an alkylene group having 2 to 8 carbon atoms; D represents a binding hand, —CO—, or an unsubstituted or substituted alkylene group having 1 to 6 carbon atoms; E represents a hydrogen atom, a lower alkyl group, an aralkyl group or an unsubstituted or substituted aryl group; m is a number of from 1 to 6; and n is a number of from 0 to 6]; k is a number of from 1 to 10; and G represents a hydrogen atom, a hydroxyl group, a carboxyl group, a sulfonate group or a phosphate group. These products are excellent in the effects of inhibiting wrinkling and smoothing wrinkles without damaging the physiological conditions of the skin.

7 Claims, No Drawings

WRINKLE-CARE PRODUCT

FIELD OF THE INVENTION

This invention relates to a wrinkle-care product, an aging-preventive cosmetic and a skin cosmetic. More particularly, it relates to aging-preventive cosmetics which is excellent in the effects for inhibiting generation of wrinkles and smoothing wrinkles.

BACKGROUND OF THE INVENTION

It is a matter of great concern for, in particular, women to maintain healthy and beautiful skin. However, skin conditions are continuously affected by various factors including humidity, UV-light, cosmetics, aging, diseases, stress, eating habits, etc. which result in various skin troubles, for example, weakening in skin functions, aging of the skin. Among these troubles, wrinkles are caused by the aging of the skin due to ageing and photo-aging due to the exposure of the skin to sunbeams. That is, cells protecting dermal fibers are reduced and contracted with ageing or due to the exposure to sunbeams. In particular, collagen fibers are seriously lost and, as a result, the degradation of the derma (i.e., true skin) and the decrease in the subcutaneous fatty tissue accelerate the skin aging, thus causing wrinkles, sags and decrease in skin elasticity.

There have been proposed various compositions and methods for inhibiting or treating these aging phenomena such as wrinkles (for example, JP-A-62-185005, JP-A-62-502546, JP-A-2-72157, JP-A-2-288822, JP-A-7-41419, JP-B-6-510542; the term "JP-A" as used herein means an "unexamined published Japanese patent application", and the term "JP-B" as used herein means an "examined Japanese patent publication"). However, none of these techniques can achieve any satisfactory wrinkle-care effect. Therefore, it has been required to develop a skin cosmetic which has an excellent wrinkle-care effect.

SUMMARY OF THE INVENTION

In view of solving the above-mentioned problems, the object of the present invention is to provide a wrinkle-care product, an aging-preventive cosmetic and a skin cosmetic which can inhibit generation of wrinkles, efficaciously smooth wrinkles and impart a good feel in use without damaging the normal physiological conditions of the skin.

Under these circumstances, the present inventors have conducted extensive studies in order to achieve the above-mentioned object. As a result, they have successfully found out that a guanidine derivative with a specific structure or an acid addition salt thereof gives an excellent wrinkle-care effect and imparts a good feel in use, thus completing the present invention.

Accordingly, the present invention provides a wrinkle-care product, an aging-preventive cosmetic and a skin cosmetic each comprising a guanidine derivative represented by formula (I) or an acid addition salt thereof:

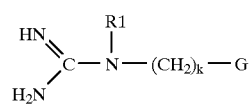

(I)

In the above formula (I), R1 represents a hydrogen atom, a lower alkyl group or —(AO)$_m$—(BO)$_n$—D—E (wherein A and B may be the same or different and each represents an alkylene group having 2 to 8 carbon atoms; D represents a binding hand, —CO—, or an unsubstituted or substituted alkylene group having 1 to 6 carbon atoms; E represents a hydrogen atom, a lower alkyl group, an aralkyl group or an unsubstituted or substituted aryl group; m is a number of from 1 to 6; and n is a number of from 0 to 6]; k is a number of from 1 to 10; and G represents a hydrogen atom, a hydroxyl group, a carboxyl group, a sulfonate group or a phosphate group.

DETAILED DESCRIPTION OF THE INVENTION

The guanidine derivative or an acid addition salt thereof to be used in the present invention is one represented by the above formula (I). The alkylene groups having 2 to 8 carbon atoms represented by A and B may be either of linear or branched one, and examples thereof include ethylene, trimethylene, tetramethylene, pentamethylene, hexamethylene and propylene groups. Among them, groups having 2 to 6 carbon atoms are preferable and groups having 2 to 4 carbon atoms (e.g., ethylene, trimethylene and propylene groups) are still preferable.

The alkylene group having 1 to 6 carbon atoms represented by D may be either of linear or branched one, and examples thereof include methylene, ethylene, trimethylene, tetramethylene, pentamethylene, hexamethylene and propylene groups.

As the lower alkyl group represented by R1, use can be made of, for example, a linear or branched alkyl group having 1 to 5 carbon atoms. Concrete examples thereof include methyl, ethyl, n-propyl, isopropyl, n-butyl, sec-butyl, tert-butyl and pentyl groups. Among them, methyl and ethyl groups are preferable.

Examples of the aralkyl group represented by E include those having 7 to 12 carbon atoms such as benzyl, phenethyl and naphthylmethyl groups.

Examples of the aryl group represented by E include phenyl and naphthyl groups and examples of the substituent thereof include an amino group which may be substituted by a lower alkyl group (e.g., methyl, etc.); a nitro group; a cyano group; a hydroxyl group; a carboxylic acid residual group which may be in the form of an ester of a lower alkyl group, a halogenated lower alkyl group or an aralkyl group; a carbamoyl group; a halogen atom (fluorine, chlorine, bromine, iodine); a lower alkyl group (methyl, ethyl, propyl, isopropyl, etc.); and a lower alkoxy group (methoxy, ethoxy, etc.).

m is a number of from 1 to 6, preferably from 1 to 4. n is a number of from 0 to 6, preferably from 0 to 4.

k is a number of from 1 to 10, preferably from 1 to 6. It is particularly preferable that G is a hydroxyl, carboxyl or phosphoric acid group.

Examples of the guanidine derivatives represented by formula (I) are as follows.

2-Hydroxyethylguanidine, 3-hydroxypropylguanidine, 4-hydroxybutylguanidine, 5-hydroxypentylguanidine, 6-hydroxyhexylguanidine, 1,1-bis(2-hydroxyethyl) guanidine, 1,1-dimethylguanidine, 1,1-diethylguanidine, 1,1-dipropylguanidine, 1,1-dibutylguanidine, 1,1-dipentylguanidine, 1,1-dihexylguanidine, 1-ethyl-1-methylguanidine, 1-methyl-1-propylguanidine, 1-butyl-1-methylguanidine, 1-methyl-1-pentylguanidine, 1-hexyl-1-methylguanidine, 3-guanidinopropanoic acid, 4-guanidinobutanoic acid, 5-guanidinopentanoic acid, 6-guanidinohexanoic acid, dihydrogen-2-guanidinoethyl phosphate, dihydrogen-3-guanidinopropyl phosphate, dihydrogen-4-guanidinobutyl phosphate, dihydrogen-5-guanidinopentyl phosphate and dihydrogen-6-guanidinohexyl phosphate.

Among these guanidine derivatives, it is particularly preferable to use 5-hydroxypentylguanidine, 3-guanidinopropanoic acid or dihydrogen-2-guanidinoethyl phosphate.

The acid to be used for forming the acid addition salt of the guanidine derivative may be either of an organic acid or an inorganic acid. Examples thereof include monocarboxylic acids such as formic acid, acetic acid, propionic acid, butyric acid, isobutyric acid, hexanoic acid, heptanoic acid, octanoic acid, nonanoic acid, decanoic acid, lauric acid, myristic acid, palmitic acid, stearic acid, acrylic acid, methacrylic acid, crotonic acid, isocrotonic acid, phenylacetic acid, cinnamic acid, benzoic acid, sorbic acid, nicotinic acid, urocanic acid and pyrrolidonecarboxylic acid; dicarboxylic acids such as oxalic acid, malonic acid, succinic acid, glutaric acid, adipic acid, pimelic acid, cork acid, azelaic acid, sebacic acid, maleic acid, fumaric acid, phthalic acid and terephthalic acid; hydroxy acids such as glycolic acid, lactic acid, malic acid, tartaric acid, citric acid and o-, m- or p-hydroxybenzoic acid; amino acids such as glycine, alanine, β-alanine, valine, leucine, phenylalanine, tyrosine, serine, threonine, methionine, cysteine, proline, hydroxyproline, pipecolic acid, tryptophan, aspartic acid, asparagine, glutamic acid, glutamine, lysine, histidine, ornithine, arginine, o-, m- or p-aminobenzoic acid and tranexamic acid; lower alkylsulfonic acids such as methanesulfonic acid and trifluoromethanesulfonic acid; arylsulfonic acids such as benzenesulfonic acid and p-toluenesulfonic acid; hydrogen halide acids such as hydrofluoric acid, hydrochloric acid, hydrobromic acid and hydroiodic acid; and inorganic salts such as perchloric acid, sulfuric acid, nitric acid, phosphoric acid and carbonic acid.

Among these compounds, a guanidine derivative represented by formula (I) or an acid addition salt thereof can be produced in accordance with the following reaction formula.

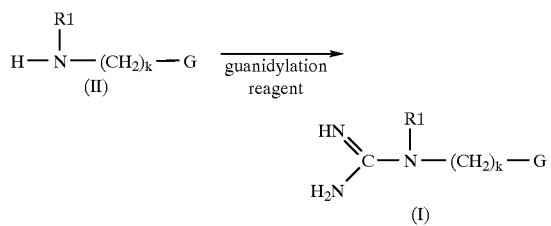

wherein k, G and R1 are each as defined above.

Namely, an amine derivative (II) is reacted with a guanidylation reagent to thereby give a guanidine derivative (I) or an acid addition salt thereof.

Examples of the amine derivative (II) to be used as the starting material include 2-aminoethanol, 3-amino-1-propanol, 4-amino-1-butanol, 5-amino-1-pentanol, 6-amino-1-hexanol, 3-N-methylamino-1-propanol, 4-N-methylamino-1-butanol, 5-N-methylamino-1-pentanol, 6-N-methylamino-1-hexanol, diethanolamine, N,N-bis-3-hydroxypropylamine, N,N-bis-4-hydroxybutylamine, N,N-bis-5-hydroxypentylamino, N,N-bis-6-hydroxyhexylamine, N-methylglycine (sarcosine), 3-aminopropanoic acid, 4-aminobutanoic acid, 5-aminopentanoic acid, 6-aminohexanoic acid, dihydrogen-2-aminoethyl phosphate, dihydrogen-3-aminopropyl phosphate, dihydrogen-4-aminobutyl phosphate, dihydrogen-5-aminopentyl phosphate and dihydrogen-6-aminohexyl phosphate.

As the guanidylation reagent, use can be made of a well-known one. Examples thereof include cyanamide, S-alkylisothiourea, o-alkylisourea, aminoiminomethanesulfonic acid, 3,5-dimethyl-1-guanylpyrazole and 1H-pyrazole-1-carboamidine.

When S-alkylisothiourea, o-alkylisourea, 3,5-dimethyl-1-guanylpyrazole or 1H-pyrazole-1-carboamidine is employed, the reaction may be performed by stirring the reactants in the presence of a base (for example, barium hydroxide, calcium hydroxide, magnesium hydroxide, sodium hydroxide, potassium hydroxide, lithium hydroxide, sodium hydrogencarbonate, sodium carbonate, aqueous ammonia; tertiary amine such as triethylamine, N,N-dimethylaniline, N,N'-dimethylpiperazine, N-methylpiperazine; pyridine) at 25 to 200° C. for 1 to 72 hours. When cyanamide is employed, the reactants may be stirred at 0 to 200° C. for 1 to 72 hours. Alternatively, they may be stirred in the presence of an acid described above regarding the acid addition salt of guanidine at 25 to 160° C. for 1 to 72 hours.

After the completion of the reaction, an acid may be added, if necessary, in a conventional manner. Thus the product can be isolated as an acid addition salt.

The guanidine derivative represented by formula (I) or an acid addition salt thereof can be produced in accordance with the method described above.

These guanidine derivatives or an acid addition salt thereof may be used either alone or as a mixture of two or more thereof. The content of the guanidine derivative or an acid addition salt thereof in the wrinkle-care product, aging-preventive cosmetic or skin cosmetic preferably ranges from 0.001 to 50% by weight, still preferably from 0.01 to 30% by weight and still preferably from 0.1 to 20% by weight, since not only the wrinkle-care effect but also an improved feel in use can be thus achieved.

It is preferable that the wrinkle-care product, aging-preventive cosmetic and skin cosmetic further contain an organic acid or an inorganic acid (phosphoric acid, sulfuric acid, hydrochloric acid, etc.), since these components contribute to the further improvement in the wrinkle-care effect.

As the organic acid, an arbitrary one may be used without restriction, so long as it is not contained in the guanidine derivative. Examples thereof include α- or β-hydroxycarboxylic acids, dicarboxylic acids, fatty acids and esters thereof. These components may be used either alone or as a mixture of two or more thereof. Examples of the organic acid include those represented by formulae (III) to (V) and esters thereof:

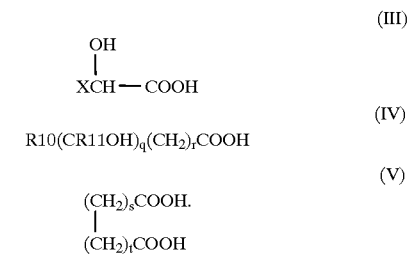

In the formula (III), X represents a hydrogen atom or $CH_3(C_fH_g)_h$ (wherein f represents an integer of from 1 to 27; g represents an integer of from 2 to 54; and h is 0 o 1).

In the formula (IV), R10 and R11 represent each a hydrogen atom or a saturated or unsaturated, linear, branched or cyclic alkyl group having 1 to 25 carbon atoms, an aralkyl group or an aryl group; q represents an integer of from 1 to 9; and r represents an integer of from 0 to 23.

In the formula (V), s represents an integer of from 0 to 9; and t represents an integer of from 0 to 23.

Concrete examples thereof include ascorbic acid, epsilon-aminocaproic acid, erythrobic acid, citric acid, succinic acid, tartaric acid, sorbic acid, dehydroacetic acid, lactic acid, urocanic acid, edetic acid, hydroxybenzenesulfonic acid, orotic acid, capric acid, glycolic acid, cerotic acid, nicotinic acid, hydroxyethanediphosphonic acid, phytic acid, fumaric acid, malic acid, levulinic acid, acrylic acid and oligomers or polymers thereof.

Examples of the fatty acid include linoleic acid, γ-linolenic acid, columbinic acid, icosa-(η-6,9,13-trienoic acid, arachidonic acid, α-linolenic acid, thymudonic acid, hexaenoic acid, isostearic acid, undecylic acid, stearic acid, palmitic acid, behenic acid, myristic acid, coconut oil fatty acid, lauric acid, lanolic acid, DHA, hydroxyfatty acids (e.g., 12-hydroxystearic acid, etc.), monoalkylphosphoric acids (e.g., cetylphosphoric acid, etc.) and dialkylphosphoric acids.

Among these organic acids and inorganic acids, it is preferable in the present invention to use dicarboxylic acids represented by formula (V). Among these, succinic acid is particularly preferable, since it can further improve the wrinkle-care effect.

The organic acids and inorganic acids may be used either alone or as a mixture of two or more thereof. The content thereof in the wrinkle-care product, aging-preventive cosmetic and skin cosmetic preferably ranges from 0.01 to 30% by weight. It is still preferable to use these acids in an amount of from 0.1 to 20% by weight, since not only an excellent wrinkle-care effect but also an improved feel in use can be achieved thereby. The weight rate of the organic acid or inorganic acid to the guanidine derivative or an acid addition salt thereof preferably ranges from 0.5:99.5 to 99.5:0.5, still preferably from 5:95 to 95:5, since the wrinkle-care effect can be further improved thereby.

The wrinkle-care product, aging-preventive cosmetic and skin cosmetic of the present invention may further contain oily components. The oily components are not particularly restricted and examples thereof include hydrocarbons (e.g., solid or liquid paraffin, crystal oil, ceresin, ozocerite, montan wax, squalane, squalerie, etc.), ester oils (olive oil, carnauba wax, lanolin, jojoba oil, glycerol monostearate, glycerol distearate, glycerol monooleate, isopropyl stearate, neopentyl glycol dicaprate, cholesterol isostearate, etc.), higher fatty acids (stearic acid, palmitic acid, etc.), higher alcohols (cetanol, stearyl alcohol, etc.) and sphingosine derivatives extracted from natural sources. These components may be used either alone or as a mixture of two or more thereof.

The content of the oily component in the wrinkle-care product, aging-preventive cosmetic and skin cosmetic of the present invention preferably ranges from 0.001 to 50% by weight, still preferably from 0.005 to 30% by weight.

The wrinkle-care product, aging-preventive cosmetic and skin cosmetic of the present invention may furthermore contain sterols. Examples of the sterols include cholesterol, provitamin $D_3$, campesterol, stigmastanol, stigmasterol, 5-dihydrocholesterol, α-spinasterol, palesterol, clionasterol, γ-sitosterol, stigmastenol, sargasterol, apenasterol, ergostanol, sitosterol, corbisterol, chondrillasterol, polyferasterol, haliclonasterol, neospongosterol, fucosterol, aptostanol, ergostadienol, ergosterol, 22-dihydroergosterol, brassicasterol, 24-methylenecholesterol, 5-dihydroergosterol, dehydroergosterol, fungisterol, cholestanol, coprostanol, dimosterol, 7-hetocholesterol, latosterol, 22-dehydrocholesterol, β-sitosterol, cholestatrien-3β-ol, coprostanol, cholestanol, ergosterol, 7-dehydrocholesterol, 24-dehydrocholestadion-3β-ol, equilenin, equilin, estrone, 17β-estradiol, androst-4-en-3β, 17β-diol, dehydroandrosterone, etc. These sterols may be used either alone or as a mixture of two or more thereof.

The content of these sterols in the wrinkle-care product, aging-preventive cosmetic and skin cosmetic of the present invention preferably ranges from 0.001 to 50% by weight, still preferably from 0.005 to 30% by weight.

The wrinkle-care product, aging-preventive cosmetic and skin cosmetic of the present invention may further contain surfactants. Examples of the surfactants include polyoxyethylene alkyl ethers, polyoxyethylene fatty acid esters, polyoxyethylene sorbitan fatty acid esters, polyoxyethylene sorbitol fatty acid esters, glycerol fatty acid esters, polyoxyethylene hardened castor oil alkyl sulfates, polyoxyethylene alkyl sulfates, alkyl phosphates, polyoxyethylene alkyl phosphates, fatty acid alkali metal salts, sorbitan fatty acid esters, glycerol fatty acid esters and alkyl glyceryl ethers. These surfactants may be used either alone or as a mixture of two or more thereof.

The content of these sterols in the wrinkle-care product, aging-preventive cosmetic and skin cosmetic of the present invention preferably ranges from 0.001 to 50% by weight, still preferably from 0.005 to 30% by weight.

The wrinkle-care product, aging-preventive cosmetic and skin cosmetic of the present invention may furthermore contain water-soluble polyhydric alcohols. The water-soluble polyhydric alcohols are those having at least two hydroxyl groups per the molecule. Examples thereof include ethylene glycol, propylene glycol, 1,3-butylene glycol, 1,4-butylene glycol, dipropylene glycol, glycerol, polyglycerols (e.g., diglycerol, triglycerol, tetraglycerol, etc.), glucose, maltose, maltitol, sucrose, fructose, xylitol, sorbitol, malttriose, threitol, erythritol and starch decomposition sugar-reducing alcohols. These alcohols may be used either alone or as a mixture of two or more thereof.

The content of these water-soluble polyhydric alcohols in the wrinkle-care product, aging-preventive cosmetic and skin cosmetic may appropriately vary depending on the type of the product. In general, the content thereof preferably ranges from 0.001 to 75% by weight, still preferably from 0.1 to 25% by weight.

The wrinkle-care product, aging-preventive cosmetic and skin cosmetic of the present invention may further contain powders. As the powders, use can be made of extender pigments (mica, talc, sericite, kaolin, nylon powder, polymethylsilsesquioxane, etc.), inorganic pigments (e.g., pearl, etc.), organic pigments (e.g., Red No. 202, Red No. 226, Yellow No. 4, aluminum chelate, etc.) and inorganic powders for UV protection (e.g., zinc oxide, titanium oxide, zirconium oxide, iron oxide, etc.). These powders may be treated with silicone compounds (e.g., methyl hydrogen methylpolysiloxane, trimethylsiloxysilicic acid, methylpolysiloxane, etc.), fluorine compounds (e.g., perfluoroalkylphosphates, perfluoroalcohols, etc.), amino acids (e.g., N-acylglutamic acid, etc.), lecithin, metal soaps, fatty acids, alkyl phosphates, etc.

The content of these powders in the wrinkle-care product, aging-preventive cosmetic and skin cosmetic may appropriately vary depending on the type of the product. In general, the content thereof preferably ranges from 0.001 to 50% by weight, still preferably from 0.005 to 30% by weight.

The wrinkle-care product, aging-preventive cosmetic and skin cosmetic of the present invention may further contain silicone compounds. As these silicone compounds, use can be made of those commonly used in cosmetics without restriction. Examples thereof include octamethylpolysiloxane, tetradecamethylpolysiloxane, methylpolysiloxane, high polymeric methylpolysiloxane, methylphenylpolysiloxane, methylpolycyclosiloxane (e.g., octamethylcyclotetrasiloxane, decamethylcyclopentasiloxane, etc.), trimethylsiloxysilicic acid and modified silicones such as polyether alkyl-modified silicone and alkyl glyceryl ether-modified silicone.

The content of these silicone compounds in the wrinkle-care product, aging-preventive cosmetic and skin cosmetic of the present invention may appropriately vary depending on the type of the product. In general, the content thereof preferably ranges from 0.001 to 50% by weight, still preferably from 0.005 to 30% by weight.

In addition, the wrinkle-care product, aging-preventive cosmetic and skin cosmetic of the present invention can contain various components commonly used in cosmetics, quasi drugs, drugs, etc., so long as the effects of the present invention are not deteriorated thereby. Examples of such the components include inorganic salts (e.g., magnesium sulfate, potassium sulfate, sodium sulfate, magnesium chloride, sodium chloride, etc.), viscosity regulating agents (e.g., polyvinyl alcohol, carboxyvinyl polymer, carboxymethylcellulose, gelatin, tragacanth gum, xanthan gum, hyaluronic acid, tuberous extract, agarose, sodium alginate, etc.), preservatives (e.g., paraben, etc.), pH regulating agents, humectants, UV-absorbers, coloring matters, medicinal components, perfumes, etc.

To sustain the normal physiological functions of the skin, the pH values of the wrinkle-care product, aging-preventive cosmetic and skin cosmetic of the present invention preferably range from 2 to 11, still preferably from 3 to 8. The skin cosmetic of the present invention can be produced by a conventional method. It may be processed into any desired form, for example, emulsions, dispersions, two-layer compositions, solutions, gels, etc. Thus the products may be in the form of lotions, milky lotions, creams, packs, foundations, etc.

The present invention provides a wrinkle-care product, an aging-preventive cosmetic and a skin cosmetic each having excellent effects of inhibiting generation of wrinkles and smoothing wrinkles and imparting a good feel in use.

EXAMPLE

To further illustrate the present invention in greater detail, and not by way of limitation, the following Examples will be given.

Example 1

The compounds (1) to (13) as specified below were employed as the guanidine derivatives or acid addition salts thereof and the wrinkle-care effects were evaluated.

Compound (1)
5-Hydroxylguanidine

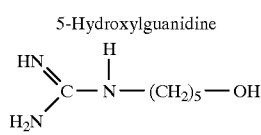

Compound (2)
3-Guanidinopropanoic acid

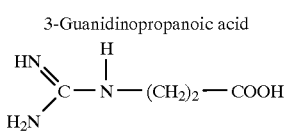

Compound (3)
Dihydrogen-2-guanidinoethyl phosphate

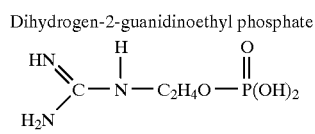

Compound (4)
3-Hydroxypropylguanidine

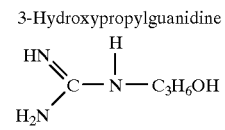

Compound (5)
Succinate

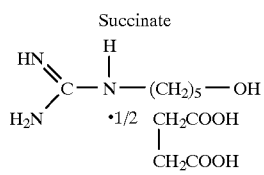

Compound (6)
Glutamate

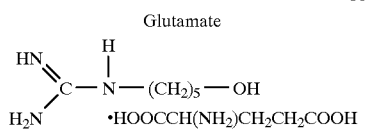

Compound (7)

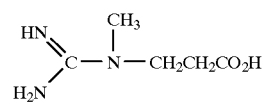

Compound (8)

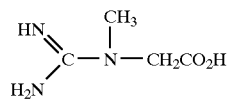

Compound (9)

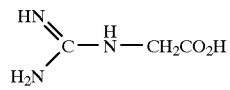

Compound (10)

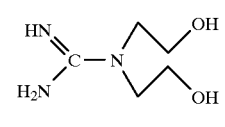

Compound (11)

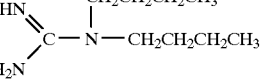

Compound (12)

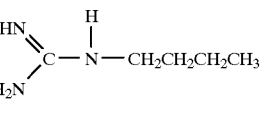

Compound (13)

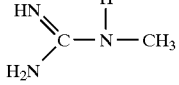

[Effects of guanidine derivatives (1) to (13) on wrinkles on hairless mice formed by UVB irradiation]

(1) Hairless mice (HR/ICR, aged 9 weeks at the initiation of the experiment) were irradiated with UVB-light thrice a week by using 6 lamps (20SE for health care, manufactured by Toshiba). The energy was measured with an UV Radiometer ("UVR-305/365D" manufactured by TOKYO OPTICAL). The single irradiation dose was regulated not to exceed 1 MED (65 mJ at 0.28 mW/cm$^2$). The irradiation was performed for 20 weeks. After confirming that the dorsal skin of the hairless mice wrinkled, the mice were divided into groups each having 8 animals. Then 100 μl portions of 2.5% solutions of the compounds (1) to (13) in a 50 vol. % aqueous solution of ethanol (water/ethanol=50/50) were applied to the mice in the test groups respectively 5 times per week continuously for 6 weeks. As a control, 100 μl of the 50% aqueous solution of ethanol alone was applied similar to the samples. After the completion of the application, the degree of wrinkles was evaluated with the naked eye in accordance with the following criteria (wrinkle index). The results are shown in Table 1.

(Wrinkle index)

1: No wrinkle.
2: Scarcely any wrinkles.
3: Some wrinkles.
4: Serious wrinkles.

(2) To further analyze the wrinkles in detail, a replica (14 mm in diameter) of the skin of each mouse was sampled by using a flexible hydrophilic vinyl silicone material (Hydrophilic Exafine). This replica was flattened and irradiated with light at an angle of 30°. Thus the rate of the shadow due to wrinkles was determined as the area rate with the use of an image analyzer. The results are shown in Table 1.

TABLE 1

| Compound | Wrinkle index | Image analyzer area rate (%) |
| --- | --- | --- |
| Control | 3.75 | 8.74 |
| (1) | 3.00 | 4.96 |
| (2) | 3.25 | 6.23 |
| (3) | 3.125 | 4.95 |
| (4) | 2.75 | 4.90 |
| (5) | 2.89 | 4.77 |
| (6) | 3.00 | 5.47 |
| (7) | 2.25 | 3.44 |
| (8) | 2.50 | 4.25 |
| (9) | 2.125 | 3.01 |
| (10) | 2.35 | 3.48 |
| (11) | 2.25 | 4.12 |
| (12) | 2.50 | 3.19 |
| (13) | 2.50 | 2.77 |

As is apparent from the results of Table 1, the wrinkles formed on the dorsal skin of the hairless mice could be smoothed by applying the guanidine derivatives or acid addition salts thereof [compounds (1) to (13)].

Example 2

An aging-preventive cream of the following composition was produced by the conventional method.

| (Component) | (wt %) |
| --- | --- |
| Stearic acid | 2.0 |
| Squalane | 2.0 |
| Cholesterol | 3.0 |
| Olive oil | 1.0 |
| Cetanol | 7.0 |
| Jojoba oil | 2.0 |
| Arginine 2-hexadecylphosphate | 2.0 |
| Polyoxyethylene-hardened (40EO) castor oil | 0.5 |
| Glycerol | 10.0 |

-continued

| (Component) | (wt %) |
| --- | --- |
| 1,3-Butylene glycol | 5.0 |
| Compound (1) | 2.0 |
| Compound (3) | 1.0 |
| Succinic acid | 1.0 |
| Purified water | the balance |
| Total | 100.0 |

Example 3

An aging-preventive milky lotion of the following composition was produced by the conventional method.

| (Component) | (wt %) |
| --- | --- |
| Palmitic acid | 0.5 |
| Olive oil | 2.0 |
| Cetanol | 1.0 |
| Jojoba oil | 5.0 |
| Sodium monohexadecylphosphate | 2.0 |
| Sorbitan monostearate | 0.5 |
| Glycerol | 15.0 |
| Ethanol | 5.0 |
| Compound (4) | 4.0 |
| Compound (2) | 2.0 |
| Lactic acid | 2.0 |
| Purified water | the balance |
| Total | 100.0 |

Example 4

An aging-preventive lotion of the following composition was produced by the conventional method.

| (Component) | (wt %) |
| --- | --- |
| Compound (1) | 7.0 |
| Compound (2) | 5.0 |
| Citric acid | 1.0 |
| 86% Glycerol | 15.0 |
| polyethylene glycol (PEG1500; Sanyo Chemical Industries) | 2.0 |
| Hyaluronic acid | 0.05 |
| Dipropylene glycol | 5.0 |
| Purified water | the balance |
| Total | 100.0 |

Example 5

An aging-preventive pack of the following composition was produced by the conventional method.

| (Component) | (wt %) |
| --- | --- |
| Polyvinyl alcohol (Gosenol EG-30; The Nippon Synthetic Chemical Industry) | 11.7 |
| 1,3-Butylene glycol | 2.5 |
| Glycerol | 1.0 |
| Titanium oxide | 1.5 |
| Compound (9) | 10.0 |
| Compound (4) | 5.0 |

| (Component) | (wt %) |
| --- | --- |
| Tartaric acid | 7.0 |
| Purified water | the balance |
| Total | 100.0 |

Example 6

An aging-preventive gel of the following composition was produced by the conventional method.

| (Component) | (wt %) |
| --- | --- |
| Polyacrylic acid (Carbopol; Goodrich) | 0.5 |
| Potassium hydroxide | 0.15 |
| Glucam | 10.0 |
| 86% Glycerol | 10.0 |
| Glycine betaine | 3.0 |
| Compound (10) | 1.5 |
| Succinic acid | 1.5 |
| Purified water | the balance |
| Total | 100.0 |

Example 7

An aging-preventive lotion of the following composition was produced by the conventional method.

| (Component) | (wt %) |
| --- | --- |
| Compound (1) | 3.0 |
| Compound (3) | 4.0 |
| 86% Glycerol | 15.0 |
| Dipropylene glycol | 5.0 |
| Purified water | the balance |
| Total | 100.0 |

Example 8

An aging-preventive lotion of the following composition was produced by the conventional method.

| (Component) | (wt %) |
| --- | --- |
| Compound (5) | 3.0 |
| Compound (10) | 0.2 |
| 86% Glycerol | 15.0 |
| Dipropylene glycol | 5.0 |
| Purified water | the balance |
| Total | 100.0 |

Example 9

An aging-preventive gel of the following composition was produced by the conventional method.

| (Component) | (wt %) |
| --- | --- |
| Polyacrylic acid (Carbopol; Goodrich) | 0.5 |
| Potassium hydroxide | 0.15 |
| Glucam | 10.0 |
| 86% Glycerol | 10.0 |
| Glycine betaine | 3.0 |
| Compound (3) | 1.5 |
| Compound (6) | 0.2 |
| Succinic acid | 1.5 |
| Purified water | the balance |
| Total | 100.0 |

Example 10

An aging-preventive milky lotion (pH 6.0) of the following composition was produced by the conventional method.

| (Component) | (wt %) |
| --- | --- |
| Palmitic acid | 0.5 |
| Olive oil | 2.0 |
| Cetanol | 1.0 |
| Jojoba oil | 5.0 |
| Sodium monohexadecylphosphate | 2.0 |
| Sorbitan monostearate | 0.5 |
| Glycerol | 15.0 |
| Ethanol | 5.0 |
| Compound (4) | 4.0 |
| Compound (9) | 0.2 |
| Lactic acid | 2.0 |
| Purified water | the balance |
| Total | 100.0 |

Example 11

An aging-preventive milky lotion of the following composition was produced by the conventional method.

| (Component) | (wt %) |
| --- | --- |
| N-(3-Hexadecyloxy-2-hydroxypropyl)-N-2-hydroxyethyldecanamide | 0.50 |
| N-(3-Hexadecyloxy-2-hydroxypropyl)-N-2-hydroxyethylhexadecanamide | 1.00 |
| N-(3-Tetradecyloxy-2-hydroxypropyl)-N-2-hydroxyethyldecanamide | 0.50 |
| Polyoxyethylene-hardened (10EO) castor oil | 1.00 |
| Methylpolysiloxane/methyl(polyoxyethylene) siloxane copolymer (SH3775C, Toray Dow Corning) | 1.00 |
| Sorbitan monostearate | 0.20 |
| Stearoylmethyltaurine sodium | 0.50 |
| Cholesterol | 0.80 |
| Cholesterol isostearate | 0.20 |
| Monocholesteryl alkenylsuccinate | 0.80 |
| Stearic acid | 0.20 |
| Palmitic acid | 0.30 |
| Myristic acid | 0.10 |
| Pentyl glycol dicaprate | 4.00 |
| Methylpolysiloxane (KF96A-500cs, Shin-Etsu Chemical) | 2.00 |
| Isostearyl alcohol | 1.20 |
| Cetyl alcohol | 1.00 |
| Glycerol | 3.50 |
| Lactic acid | 0.20 |
| Sodium lactate | 0.30 |
| Compound (11) | 5 |
| Preservative | q.s. |

| (Component) | (wt %) |
|---|---|
| Perfume | q.s. |
| Purified water | the balance |
| Total | 100.0 |

Example 12

An aging-preventive cataplasm of the following composition was produced by the conventional method.

| (Component) | (wt %) |
|---|---|
| α-Monoisostearyl glyceryl ether | 1.00 |
| Pentyl glycol neocaprate methylpolysiloxane | 4.00 |
| Glycerol | 35.00 |
| Purified water | 15.80 |
| Sodium polyacrylate | 5.50 |
| Aluminum potassium sulfate | 1.00 |
| Aqueous solution of polyacrylate (10%) | 15.00 |
| Light silicic anhydride | 2.00 |
| Compound (1) | 5 |
| Compound (9) | 5 |
| Purified water | the balance |
| Total | 100.0 |

While the invention has been described in detail and with reference to specific embodiments thereof, it will be apparent to one skilled in the art that various changes and modifications can be made therein without departing from the spirit and scope thereof.

What is claimed is:

1. A method for treating wrinkles comprising administering to the skin of a subject in need thereof a wrinkle-treating effective amount of a guanidine derivative represented by formula (I) or an acid addition salt thereof:

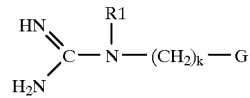

wherein R1 represents a hydrogen atom, a lower alkyl group or $-(AO)_m-(BO)_n-D-E$ (wherein A and B may be the same or different and each represents an alkylene group having 2 to 8 carbon atoms; D represents a binding hand, $-CO-$, or an unsubstituted or substituted alkylene group having 1 to 6 carbon atoms; E represents a hydrogen atom, a lower alkyl group, an aralkyl group or an unsubstituted or substituted aryl group; m is a number of from 1 to 6; and n is a number of from 0 to 6); k is a number of from 1 to 10; and G represents a hydrogen atom, a hydroxyl group, a carboxyl group, a sulfonate group or a phosphate group.

2. The method as claimed in claim 1, wherein the guanidine derivative or an acid addition salt thereof is administered in a composition and is contained in an amount of from 0.001 to 50% by weight of the composition.

3. The method as claimed in claim 1 which further comprises coadministering an organic acid or an ester thereof.

4. The method as claimed in claim 3, wherein the organic acid or ester thereof is coadministered in a composition and is contained in an amount of from 0.001 to 30% by weight of the composition.

5. The method as claimed in claim 1, wherein said guanidine derivative is represented by the formula:

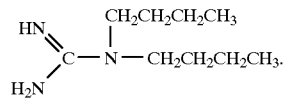

6. The method as claimed in claim 1, wherein said guanidine derivative is represented by the formula:

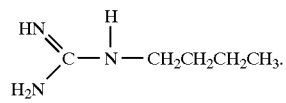

7. The method as claimed in claim 1, wherein said guanidine derivative is represented by the formula:

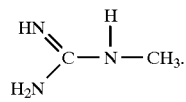

* * * * *